United States Patent [19]

El Khoury

[11] Patent Number: 5,994,330

[45] Date of Patent: Nov. 30, 1999

[54] TOPICAL APPLICATION OF MUSCARINIC AGENTS SUCH AS NEOSTIGMINE FOR TREATMENT OF ACNE AND OTHER INFLAMMATORY CONDITIONS

[76] Inventor: Georges F. El Khoury, 1561 Ramillo Ave., Long Beach, Calif. 90815

[21] Appl. No.: 09/188,328

[22] Filed: Nov. 9, 1998

[51] Int. Cl.$^6$ .................................................. A01N 57/00
[52] U.S. Cl. ....................... 514/123; 514/123; 514/859; 514/855; 514/289; 514/912; 514/78.04; 424/401
[58] Field of Search .......................... 424/401; 536/55.1; 514/912, 78.04, 289, 859, 123, 855

[56] References Cited

U.S. PATENT DOCUMENTS

| | | | |
|---|---|---|---|
| 3,275,510 | 9/1966 | Magid et al. | 514/946 |
| 4,416,886 | 11/1983 | Bernstein | 424/260 |
| 4,626,539 | 12/1986 | Aungst et al. | 514/282 |
| 4,871,750 | 10/1989 | Roberts | 514/328 |
| 4,897,260 | 1/1990 | Ross et al. | 424/59 |
| 5,069,909 | 12/1991 | Sharma et al. | 424/499 |
| 5,540,918 | 7/1996 | Castillo et al. | 424/78.04 |
| 5,834,480 | 11/1998 | El Khoury | 514/289 |

FOREIGN PATENT DOCUMENTS

WO 9213540  8/1992  WIPO.

OTHER PUBLICATIONS

J. L. Joris et al., *Anesth. Analg.*, Opioid Analgesia At Perhipheral Sites: A Target for Opioids Released During Stress and Inflammation? 66:1277–81 (1987).

H. Bouaziz, MD et al., *Anesth Analg.*, "Postoperative Analgesia from Intrathecal Neostigmine in Sheep," 80:1140–4 (1995).

G. Lauretti, MD et al., *Anesth Analg.*, "Dose–Response Study of Introthecal Morphine Versus Intrathecal Neostigmine, Their Combination . . . " 82:1182–7 (1996).

S. Abram, MD et al., *Anesth Analg.*, "Intrathecal Acetyl Cholinesterase Inhibitors Produce Analgesia That is Synergistic with Morphine and Clonidine in Rats," 81:501–7 (1995).

C. Stein, M.D. et al., *New England Journal of Medicine*, vol. 325, No. 16 "Analgesic Effect of Intraarticular Morphine After Arthroscopic Knee Surgery," pp. 1123–1126.

T. Yaksh, Ph.D. et al., *Anesthesiology*, "Studies on the Safety of Chronically Administered Intrathecal Neostigmine Methylsulfate in Rats and Dogs," V 82. No. 2, Feb. 1995.

"Morphine—A 'Local Analgesic,'" International Association for the Study of Pain, vol. III.

G. Lauretti, MD et al., *Anesth Analg* "The Effects of Intrathecal Neostigmine on Somatic and Visceral Pain: Improvement by Associate with a Peripheral Anticholinergic," 81:615–20 (1996).

D. Hood, M.D., et al., *Anesthesiology*, "Phase I Safety Assessment of Intrathecal Neostigmine Methylsulfate in Humans," V 82., No. 2, Feb. 1995 pp. 331–342.

Goodman & Gillman's, *The Pharmacological Basis of Therapeutics*, 9th Ed., McGraw–Hill pp. 141–175.

(List continued on next page.)

*Primary Examiner*—Keith D. MacMillan
*Assistant Examiner*—Vickie Kim
*Attorney, Agent, or Firm*—Millen, White, Zelano, Branigan, P.C.

[57] ABSTRACT

Treatment of acne through topical administration is an aspect of the present invention. Specifically, muscarinic agents may be applied in any therapeutically acceptable carrier including gels, creams, lotions, and sprays. Therapeutic effects observed with the present invention include decrease in redness, swelling, and inflammation. Treatment of other inflammatory conditions is also disclosed. Treatment of suitable conditions in accordance with the present invention results in significant improvements in healing of those conditions.

22 Claims, 1 Drawing Sheet

OTHER PUBLICATIONS

Tennant et al. Abs. of Int. Pharm. Abs. (Lancet) v. 342 (Oct. 23, 1993) p. 1047–1048.

Letters to the Editor, *The Lancet,* vol. 342, Oct. 23, 1993, pp. 1047–1048.

C. Stein, M.D., "The Control of Pain in peripheral Tissue by Opioids," *Mechanisms of Disease,* vol. 332, No. 25, pp. 1685–1690, (1995).

C. Williams, Intrasite Gel: A Hyrogel Dressing, Product Focus (3–page article).

Remington Pharmaceutical Sciences 18th ed., Chapter 87, "Medicated Applications," pp. 1596–1614 (1990).

C. Stein, "Peripheral and Non–Neuronal Opioid Effects," *Current Scient Ltd.,* 1–85922–136–X ISSN 0952–7907, pp. 347–351.

S. Moiniche, et al., "Peripheral Antinociceptive Effects of Morphine After Burn Injury," *Acta Anaesthesiologica Scandinavica,* ISSN 0001–51772, pp. 710–712 (1993).

C. Stein, "Peripheral Mechanisms of Opioid Analgesia," *Anesth Analg* 1993; 76:182–92.

C. Stein et al., "Peripheral Opioid Receptors," *Annals of Medicine* 17:219–221 (1995).

TOPICAL APPLICATION OF MUSCARINIC AGENTS SUCH AS NEOSTIGMINE FOR TREATMENT OF ACNE AND OTHER INFLAMMATORY CONDITIONS

BACKGROUND OF THE INVENTION

The present invention is direction to the treatment of acne and other inflammatory conditions. More specifically, in some embodiments this invention relates to methods for treating acne which methods comprise the topical application of muscarinic agents such as neostigmine. Treatment in accordance with the present invention results in improved healing in the treated area.

Acne is one example of inflammatory conditions which may be treated in accordance with the present invention.

Acne is a multi factorial disease affecting the sebaceous follicle and characterized by papules, pustules, and scars. Acne affects nearly 90% of 16-year old boys and girls but is clearly no longer a problem confined to teenagers. Recently for this condition, referral for specialists' opinions have significantly increased among people over the age of 20. It has been realized that simple attention to hygiene is no longer sufficient, and antiseptic washes so popular some years ago are now perceived as ineffective by many sufferers and most clinicians.

During puberty, elevated androgen levels stimulate the sebaceous glands to enlarge and produce increased amounts of sebum in the sebaceous follicle. Subsequent abnormal keratinization with hyperkeratosis of the follicular epithelium leads to obstruction of the duct by horny plaque. The blocked duct becomes clogged with a dense material composed of sebum and keratinous debris forming a micro comedo, a precursor of the acne lesion. The excess sebum in the micro comedo also provides an anaerobic growth medium for *Propionibacterium acnes*. Lipase from the bacteria hydrolyzes sebum triglycerides into free fatty acids that are both comedogenic and proinflammatory. *Propionibacterium acnes* also secretes chemotactic factors that attract neutrophils. Lysosomal enzyme released from the neutrophils rupture the follicle wall releasing proinflammatory mediators including keratin and lipids into the surrounding dermis. Inflammatory papules appear as a result. Further inflammation with macrophages and foreign body reactions lead to cysts and nodules. The key features of the pathogenesis of acne can be characterized as 1) increased sebum production, 2) follicular corynekeratinization, 3) bacterial proliferation, and 4) inflammation.

Effective management of acne can be accomplished by addressing the four key features of the pathogenesis. Topical therapy is usually the first choice for patients with mild-to-moderate inflammatory acne. The use of topical therapy minimizes potential side effects associated with the use of systemic agents. Topical therapies include benzoyl peroxide, which is the most commonly used non-prescription acne medication. It is an important antibacterial oxidizing agent that can decrease the number of *Propionibacterium acnes* and frequently the amount of free fatty acids. Benzoyl peroxide is the first line of monotherapy for mild acne and it is available in over-the-counter preparations. Benzoyl peroxide is applied once or twice daily and patients often experience mild redness and scaling of the skin during the first week of usage.

Tretinoin is the most effective topical comedolytic agent, decreasing the cohesiveness of follicular epithelial cells, and thereby inhibiting the formation of microcomedones and increasing cell turnover resulting in expulsion of existing comedones. This agent also decreases the thickness of the stratum corneum and potentiates the penetration of topical antibiotic agents. Tretinoin therapy comprises once daily application. Mild redness and peeling are a part of the therapeutic effect of the medication but can result in reduced patient compliance. Patients should be made aware that improvement may take as long as 6 to 12 weeks, and that flare-ups of acne can occur during the first few weeks of therapy. In addition, it is extremely important that patients avoid excessive exposure to the sun during treatment.

Mild inflammatory acne lesions can also be treated with topical antibiotics including erythromycin ointment, clindamycin solution, and meclocycline cream. The primary action of the antibiotics is to reduce the population of *Propionibacterium acnes* in the sebaceous follicle and thereby suppress the free fatty acid production. The effectiveness of topical antibiotics in the treatment of acne is limited by their low lipid solubility and subsequent difficulty in penetrating sebum-filled follicles. Topical antibiotics are applied twice daily.

Patients with moderate to severe inflammatory acne often require oral antibiotics in addition to topical therapy. The most commonly prescribed agents include tetracycline, erythromycin, minocycline, and doxycycline. Treatment is usually maintained for several months. Side effects include the overgrowth of nonsusceptible organisms including Candida, which can produce vaginal and oral yeast infections.

Patients with severe inflammatory acne unresponsive to other therapy may require treatment with oral isotretinoin. Isotretinoin is a compound related to vitamin A, and is the only agent that decreases sebum production and reverses the abnormal epithelial formation process. This agent can also decrease the population of *Propionibacterium acnes* in the sebaceous follicle. Duration of therapy is usually 20 weeks, and the satisfactory response rate is quite high. Treatment is often accompanied by many side effects, however, including dry skin, pruritus, epistaxis, and photosensitivity, as well as hypertriglyceridemia, abnormal liver function tests, electrolyte imbalances, and elevated platelet counts. Most serious though, is the teratogenic effect of isotretinoin. Use of isotretinoin during pregnancy is absolutely contraindicated. So serious is the potential for death or teratogenic effects to a fetus, isotretinoin is practically contraindicated in women of child-bearing age. Use of isotretinoin must be accompanied by a guarantee by the patient that conception will be avoided at any and all costs.

Because acne is a multi factorial disease which is manifest to varying degrees, it is important for the physician to assess the patient to attempt to find therapies which will be helpful to the patient without causing major side effects. All of the current conventional treatments are associated with some degree of adverse side effects that limit their usefulness. Consequently, there is a need for a drug that eliminates acne without side effects.

As discussed above, the formation of acne is frequently associated with inflammation. During the inflammatory process, white blood cells are attracted to the area of the lesion, and play a crucial role in fighting the infection. Other local infections are characterized by similar inflammatory processes. In addition, burns also trigger the body's inflammatory response.

Peripheral Analgesia Using Opioid Agents

In the past, administration of opioids has been directed at targeting opioid receptors in the central nervous system (CNS). In addition to their presence in the CNS, opioid receptors have been found on sensory nerves in inflamed subcutaneous tissue. This finding was reported in Stein et al., "Peripheral effect of fentanyl upon nociception in inflamed tissue of the rat," *Neurosci Lett,* 84:225–228 (1988), and in Stein et al., "Antinociceptive effects of mu- and kappa-agonists in inflammation are enhanced by a peripheral opioid receptor-specific mechanism of action," *Eur. J. Pharmacol.,* 155:255–264 (1988). Small doses of opioids, when applied locally or topically in inflamed areas outside of the central nervous system, can produce local analgesic effects by interacting with the opioid receptors on peripheral sensory nerves and producing local analgesia. This finding was discussed in Stein et al., "Opioids as novel intraarticular agents in arthritis," In: *Progress in Pain Research and Management,* Fields, H. L., and Liebeskind, J. C., eds., 1:289–296, IASP Press, Seattle (1994). A practical application of this phenomena is presented in U.S. Pat. No. 5,589,480 to ElKhoury et al., wherein the topical application of an opioid analgesic agent to alleviate pain is disclosed. Reference is also made to the present inventor's copending U.S. patent applications Ser. Nos. 08/741,743, 08/732,594, 09/028,117, 09/083,431, and 08/874,254, which are hereby incorporated by reference as though set forth in full herein.

Peripheral opioid effects are not initially apparent in normal tissue, but do become apparent within minutes to hours at the site of inflammation. It is believed that the reason for the pain relief is that opioids can gain easier access to neuronal opioid receptors during inflammation as a result of the disruption of the perineurium (which is normally an impermeable sheath encasing the peripheral nerve fiber). Further, the number of peripheral sensory nerve terminals is increased in inflamed tissue and a phenomenon known as sprouting occurs in which the number of fibers increases significantly within inflamed tissued. The sprouting results in a subsequent increase in the number of morphine receptors that are peripherally accessible to locally-applied opioids.

In addition to their presence in the peripheral nervous system, opioid receptors have been identified in the immune system as well. Specific opioid receptors, identified as $\mu_3$ receptors, have been identified on white blood cells, including macrophages and peripheral blood granulocyites, both of which are involved in the immune response in humans. In addition, it has been shown that some lymphocytes, as well as some monocytes and macrophages, produce endogenous opioid peptides. These findings have led some researchers to suggest a neural-immune link. However, the manner in which these two systems interact is still quite unclear. A review of opioid receptors in immunocytes and neurons is presented in *Advances in Neuroimmunology* Vol. 4, pgs. 69–82 (1994), the entire content of which is hereby incorporated by reference as though set forth in full herein. The role of immune processes in peripheral opioid analgesia is presented in Chapter 27 of *The Brain Immune Axis and Substance Abuse* (Sharp, B. et al., eds.) (Plenum Press, New York, 1995), the entire content of which is hereby incorporated by reference as though set forth in full herein.

Unfortunately, morphine and other opioid drugs have a number of severe side effects which hamper their wide spread use and acceptance by both physicians and patients. These side effects include: addiction, nausea, inhibition of breathing, somnolence and dysphoria, all of which are mediated by morphine's action within the brain. It is still the current belief that narcotics ingested or injected will cross to the blood stream and from there go to the brain where there are morphine receptors. At that time, the narcotics are believed to attach to these morphine receptors and create a dullness of the pain but with all of the side effects described above. Of course, the worst potential effect is the addiction that can occur if the morphine is used beyond a few days or weeks on a continuous basis.

Because of the fear of addiction, the use of morphine as an analgesic has been restricted. In addition, major research efforts have been directed toward the development of morphine-like drugs that act within the brain but are devoid of the side effects. The market for these other drugs has never fully materialized because these drugs were not perceived as having the same analgesic properties of morphine and because typically these drugs were not produced to be both available in oral and injectable formats.

In the past ten years, the intraspinal method of treating pain has been extensively developed but, as more extensive use was made of this technique, a number of serious problems developed. The first problem is that the intraspinal method of treatment requires a spinal tap which of course necessitates the use of a needle to the spinal cord. The second problem results from the first in that if it is necessary to use the intraspinal method over a period of time, such as two or three weeks, medication must be injected into the spine for this period of time and the continuous needle sticks into the spine has potential hazards. Further, if it is necessary to use the intraspinal method over time, even though the dosage is substantially less compared to oral or intravenous dosages, there is still a high potential for addiction and with such addiction the resultant problems of withdrawal and its associated side effects.

Although intraspinal application of narcotics is still used to alleviate pain after surgery, this technique has the limitations with the potential for addiction as described above. In addition, it has been determined that with frail patients there is the risk that the patient can stop breathing and there have been a number of cases of respiratory arrest after the administration of narcotics using the intraspinal technique. Further, the intraspinal technique of administering narcotics creates difficulty with male patients and especially with elderly male patients in that there can be problems with urination and with consequent problems of urine retention. Finally, this intraspinal technique produces a significant itching problem as a side effect.

In recent studies, it was discovered that opioid receptors may also be located in other peripheral tissues. This was reported in Stein, C. et al., Peripheral effect of fentanyl upon nociception in inflamed tissue of the rat. Neurosci. Lett. 84:225–228 (1988), and in Stein, C. et al., Antinociceptive effects of mu- and kappa-agonists in inflammation are enhanced by a peripheral opioid receptor-specific mechanism of action. Eur. J. Pharmacol. 155:255–264 (1988). Subsequently, animal experiments were performed in Dr. Stein's laboratory characterizing peripheral opioid receptors and their activation by morphine and other opioid drugs. Stein, C., et al., N. Engl. J. Med. 325:1123–1126 (1991) also reported the analgesic effect of intraarticular morphine after arthroscopic knee surgery. These results were reviewed in Stein, C., Peripheral mechanisms of opioid analgesia. Anesth. Analg. 76:182–191 (1993), and in Stein, C., Lehrgerger, K., Yassouridis, A., Khoury, G.: Opioids as novel intraarticular agents in arthritis. In: Progress in Pain Research and Management, Fields, H. L., Liebeskind, J. C., eds., 1:289–296, IASP Press, Seattle (1994). A most important determination from these various studies is that the doses of the drugs required to produce analgesia in the peripheral tissues are extremely small and therefore devoid of the above mentioned side effects produced by dosages sufficient to operate on the brain.

In addition, it was determined that the endogenous ligands of peripheral opioid receptors (endorphins, the body's own pain killers) are located within the inflamed tissue. It was also determined that the endorphins can produce intrinsic analgesia within peripheral tissues both in animals and in humans (Stein (1993), ibid.). It was further noted that the peripheral opioid effects were more pronounced in inflamed than in non-inflamed tissues.

Severe pain caused or accompanied by inflammation in skin is a particularly intractable problem, because the underlying reasons for it tend to be both long-term and yet not inherently life-threatening, e.g., shingles and various kinds of burns, both of militate against the chronic systemic use of opioid agents. This led to initial investigations into whether it might be possible to be able to induce effective opioid analgesia in such cases without negative systemic opioid administration effects.

Initially, it was thought that it would be necessary to inject the morphine into an inflamed area since the inflammation activates the opioid receptors and it was also believed that the morphine had to be in an enclosed space to stay in contact with the area that was inflamed. The initial experiments were conducted in conjunction with arthroscopic surgery of the knee and a number of patients were medicated after arthroscopic surgery with injected morphine. These patients were medicated either with morphine alone, with a local anesthetic such as Marcaine or a combination of Marcaine and 1 mg of morphine. It was shown that patients receiving morphine into the joint had significantly more pain relief than patients receiving the same dose intravenously (demonstrating a local effect) and that this effect was mediated by intraarticular opioid receptors. Furthermore, patients who received just Marcaine after the surgery had relief but the relief typically did not extend beyond 12 hours or at most the next day after surgery. The patients who received Marcaine plus one mg of morphine in the knee had much better relief extending for at least twice as long as those that received Marcaine alone. See Stein et al. (1991).

At this point, it was still thought that it was necessary to keep the morphine in a closed space, such as in a knee, and the results of such controlled clinical studies reporting analgesia produced by morphine injected into the knee joint were reported in Stein et al., N. Engl. J. Med., 325: 1123–1126 (1991); Comment in N. Engl. J. Med., 325:1168–1169 (1991) and Khoury et al., Anesthes. 77:263–266 (1992). These studies have been replicated by several other groups throughout the world, but this application of morphine was relatively restricted to the practice of orthopedic surgeons using the morphine injected into a joint after arthroscopic surgery and further progress was restricted because it was thought that the morphine had to be contained in the closed space so as to keep the medication in close contact with the inflamed area.

Thus, there was a body of studies determining that opioid receptors were found in various peripheral tissues and suggesting that peripheral opioid effects would be more pronounced in inflamed than in non-inflamed tissues; however, there was no specific determination of how to provide an analgesic effect, using narcotics such as morphine, other than by injection of morphine into a closed space such as a joint. None of these reports discussed the possibility that pain relief could be topically induced in skin, whether inflamed or not, nor was it even known whether peripheral opioid receptors are present in human skin.

Nevertheless, while the need for adequate treatment and relief of pain in inflamed skin was evident, there was a lack of evidence that human skin contained peripheral opioid receptors, and there was doubt whether topical administration in the absence of the enclosed conditions akin to administration into the intra-articular space would work. Thus, the inventors of U.S. Pat. No. 5,589,480 conceived and developed a method of carrying out the concept of effecting topical local analgesia in inflamed skin with opioid agents.

The fact that the opioid effects are more pronounced in inflamed than in non-inflamed tissues is a considerable advantage considering that most painful conditions are associated with inflammation, for example, cancer, arthritis, trauma, post-operative pain, skin lesions, etc. The work disclosed in U.S. Pat. No. 5,589,480 demonstrated that extremely small systemically inactive doses of both conventional opioid drugs such as morphine, as well as other opioid agents, can produce potent analgesic effects after local application to inflamed skin in peripheral tissue. U.S. Pat. No. 5,589,480 discloses a method and preparation for a topical application of an opioid drug, such as morphine, for a direct activation of the peripheral opioid receptors on the surface of inflamed skin, without any substantial transdermal or transmucosal systemic delivery of the opioid.

Without wishing to be bound by theory, it is believed that the inflammatory process in peripheral tissue is associated with an increase in sensitivity to the antinociceptive effects of opioid agents, perhaps by activation of opioid receptors located on primary afferent neurons. This may occur by one or more means, e.g., de novo synthesis of opioid receptors which increases the number of receptors; axonal transport of pre-existing receptors to peripheral nerve terminals increasing their concentration and thus sensitivity; some other means of activation of pre-existing neuronal opioid receptors by the inflammatory process. See, e.g., Stein, C., Peripheral and non-neuronal opioid effects. Curr. Opin. Anaesth. 7:347–351 (1994). In addition, again without wishing to be bound by theory, inflamed skin is generally more permeable to topically-administered agents, because the inflammatory process destroys Schwann cells in the epidermis, leading to further exposure of the nerve terminals; inflammation also causes edema, which results in loss of integrity of the epidermis, making the nerve terminals more accessible to topical agents.

Although U.S. Pat. No. 5,589,480 demonstrated the effectiveness of topically-applied opioid analgesics without systemic delivery in inflamed skin, the treatment of peripheral pain in the case of non-inflamed skin faced the additional hurdles of lesser skin permeability, which thus required the addition of skin penetration enhancers and thus risked unwanted systemic delivery, and also did not have the same basis for expecting a successful outcome, i.e., that the inflammatory process in peripheral tissue is associated with an increase in sensitivity to the antinociceptive effects of opioid agents, e.g., due to an increase in the number and/or sensitivity of opioid receptors at peripheral nerve terminals induced by the inflammatory process. Therefore, it could not be predicted whether or how topical analgesia could be induced in non-inflamed skin or mucosa, at least without effecting systemic transdermal or transmucosal delivery as well. Moreover, it was desired to improve, if possible, the effectiveness of topical opioid analgesia induced in inflamed skin or mucosal tissue, without effecting systemic delivery of the opioid agents.

As expected, application of the pharmaceutical preparations in accordance with those disclosed in U.S. Pat. No. 5,589,480, which comprised, e.g., morphine sulfate in a simple pharmaceutically acceptable topical excipient, e.g., water, saline or hydrophilic gel such as KY Jelly, when applied to intact, non-inflamed skin in a patient suffering from non-inflammatory skin pain such as peripheral neuropathy, did not work. However, when skin-specific penetration enhancers are added to the topical formulation, it was found that even pain arising in non-inflamed skin could be successfully treated with topical, local analgesic agents which affect peripheral opioid receptors in the absence of delivery of clinically effective central nervous system levels. Moreover, these skin penetration enhancers were surprisingly shown to improve the effectiveness of local opioid analgesic agents which bind to opioid receptors in the treatment of pain in inflamed skin or mucosal tissue without the concomitant delivery of substantial amounts of the analgesic agent into the systemic circulation. This invention is fully disclosed in U.S. Ser. No. 09/028,117. The analgesic effect was thus potentiated by topically administering to a patient in need of such treatment a topically effective amount of an analgesic agent, which amount is systemically ineffective for induction of analgesia, admixed with a skin- or mucosa-specific penetration enhancer, such as, e.g., lecithin, and a pharmaceutically acceptable excipient for topical administration, preferably whereby effective analgesia in the non-inflamed skin or mucosal tissue is induced in the substantial absence of transdermal or transmucosal delivery of the opioid analgesic agent to the systemic circulation.

Peripheral Muscarinic Analgesia

L. C. Yang et al., Anesthesiology 88:334–339 (1998) discloses inducing post-operative analgesia by intra-articular administration of neostigmine in patients undergoing knee arthroscopy, using a counterpart of the method disclosed in Stein et al. (1991). Neostigmine is an acetylcholinesterase inhibitor; it was postulated to induce analgesia by a variety of pathways, presumably via induction of peripheral cholinerigic antinociception by elevating endogenous acetylcholine available to peripheral muscarinic receptors. Systemic administration of neostigmine through the spinal or epidural route of administration has been shown to have dose-related side effects similar to opioids, such as nausea, vomiting and pruritus.

It therefore was deemed desirable to provide an additional analgesic in the pharmaceutical arsenal of antinociceptives, by providing an effective topical method of treating pain via the muscarinic receptor pathway of analgesia, without the negative effects of systemic neostigmine administration. The work disclosed in U.S. application Ser. No. 09/083,431 demonstrated that small systemically inactive doses of neostigmine, can produce potent analgesic effects after local application to inflamed skin in peripheral tissue. Application Ser. No. 09/083,431 discloses a method and preparation for a topical application of a muscarinic drug, such as neostigmine, for a direct activation of the peripheral muscarinic receptors on the surface of inflamed skin, without any substantial transdermal or transmucosal systemic delivery.

Treatment of Acne with Opioid Analgesic Agents

U.S. Ser. No. 08/874,254 disclosed that topical application of small systemically inactive doses of opioid analgesic agents surprisingly were effective for the treatment of acne. However, especially in the case of minors suffering from acne, this treatment requires use of a controlled substance. Thus, it would also be desirable to provide an additional non-narcotic, non-teratogenic agent in the pharmaceutical arsenal of acne treatments, by providing another effective topical method of treating acne, e.g., via the muscarinic receptor pathway, without the negative effects of systemic neostigmine administration.

SUMMARY OF THE INVENTION

In accordance with the present invention, it has been surprisingly found that topical application of muscarinic agents results in a significant reduction in acne lesions. Doses of muscarinic agents used in accordance with the present invention are very small, such that they produce no significant systemic effect. Further, in accordance with the present invention, the muscarinic agents may be applied in carrier vehicles which do not further aggravate acne lesions. The compositions of this invention thus comprise a topically-effective amount of an agent which affects peripheral muscarinic receptors, which amount is systemically ineffective for induction of analgesia, optionally admixed with a skin-penetration enhancer, e.g., lecithin, and a pharmaceutically acceptable excipient for topical administration, preferably whereby the therapeutically effective treatment is induced in the inflamed or non-inflamed acne-affected skin in the substantial absence of transdermal delivery of the muscarinic agent to the central nervous system.

The present invention is also directed to effectively treating inflammation of the skin and effectively treating topical bacterial infections and inflammation associated therewith.

The present invention is further directed to effectively treating acne through the topical application of muscarinic agents without the side effects associated with prior acne treatments.

The present invention is further directed to effective relief of the symptoms of acne through the use of topical muscarinic agent administration, thereby effectively reducing the acne lesions.

The present invention is achieved by the provision of methods of treating acne in a patient in need of such treatment comprising the topical administration of a therapeutically-effective amount of a composition comprising a muscarinic agent. Preferably, the composition comprises a gel or cream, which is preferably administered by spreading the gel or cream onto the affected area. In other preferred embodiments, the composition comprises a liquid, which is preferably administered by spraying onto the affected area. In general, with continued application on a periodic basis, in invention provides therapeutic benefit without any of the typical side effects such as nausea, vomiting and itching which would typically result if muscarinic agents such as neostigmine were received by the brain.

The quantities of the applied muscarinic agent described herein in the Figures and in the Examples are illustrative only and it is to be appreciated that lesser and greater quantities may be used, which can be routinely optimized by the skilled worker. In general, amounts analgesically or acne-therapeutically equivalent to 0.05 to 0.1 mg of neostigmine applied to an area of 6 in$^2$, or 0.005 mg/kg of body weight, are preferred. However, the quantity of muscarinic agent used in the topical application of the present invention is typically a small fraction of the typical dosage used in other methods of treatment using these agents, e.g., intravenous administration for the reversal of muscle relaxant, e.g., curare, paralysis during surgery. The muscarinic agent preferably comprises neostigmine. In preferred embodiments, the acne comprises inflammatory acne. In other preferred embodiments, the acne comprises non-inflammatory acne.

The present invention is further achieved by the provision of methods of treating local inflammation of the skin comprising a bacterial infection, the method comprising the administration of a therapeutically-effective amount of a muscarinic agent. Preferably, the local inflammation of the skin comprises a Staphylococcus infection.

The present invention is further achieved by the provision of a method of treating skin disorders involving the sebaceous glands and follicles in humans comprising applying a therapeutically-effective amount of a muscarinic agent.

The present invention is further achieved by the provision of a method of treating acne in a patient in need of such treatment comprising the topical administration of a therapeutically effective amount of a composition comprising a muscarinic agent, wherein said administration is achieved via a topical dressing.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

As a specific example, 2 mg of neostigmine and 2700 mg of lecithin may be diluted in 120 cc of saline to form the spray 12. The neostigmine/lecithin is initially provided as a solution of 16.8 mg/cc, whereby the final spray solution contains 2 mg in a total of 120 cc. Thus, the final concentration of neostigmine in the spray is 0.0168 mg/cc. The specific application may result in approximately 0.1 mg of neostigmine in solution to cover approximately a 6×6 square inch area.

Figure 1:
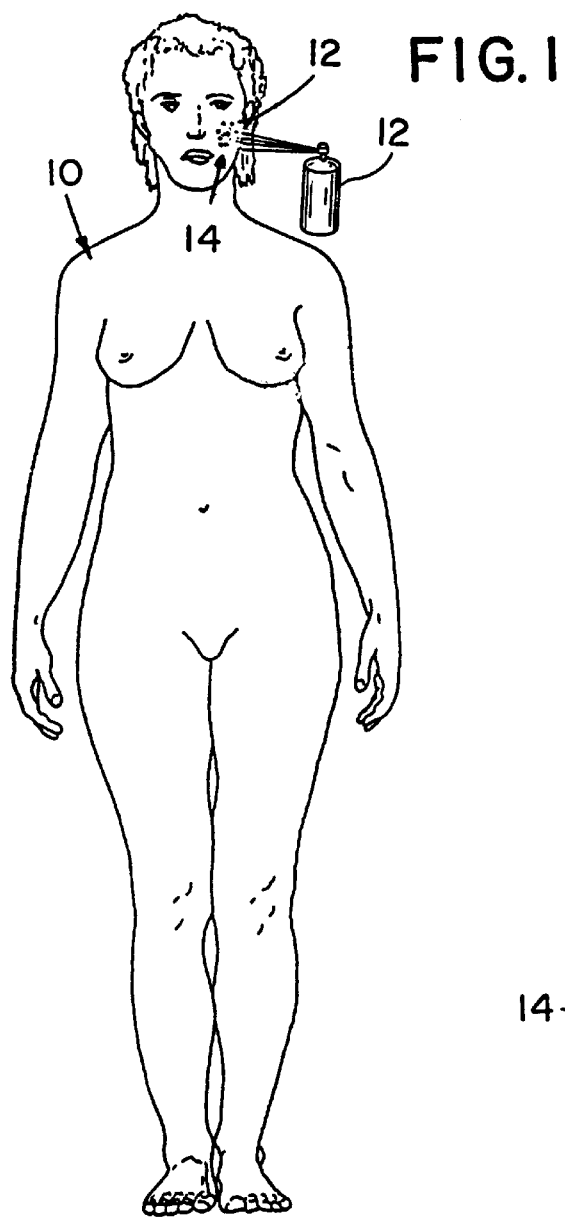
FIG. 1 illustrates a method and apparatus of the present invention and specifically shows a patient 10 receiving a topical application of an agent which affects muscarinic receptors, such as neostigmine, optionally admixed with a skin penetration enhancer, using a spray 12. In particular, a small quantity of the neo-stigmine solution is then sprayed onto an acne-affected area 14 on a patient 10 to provide the particular treatment described above.
Figure 2:
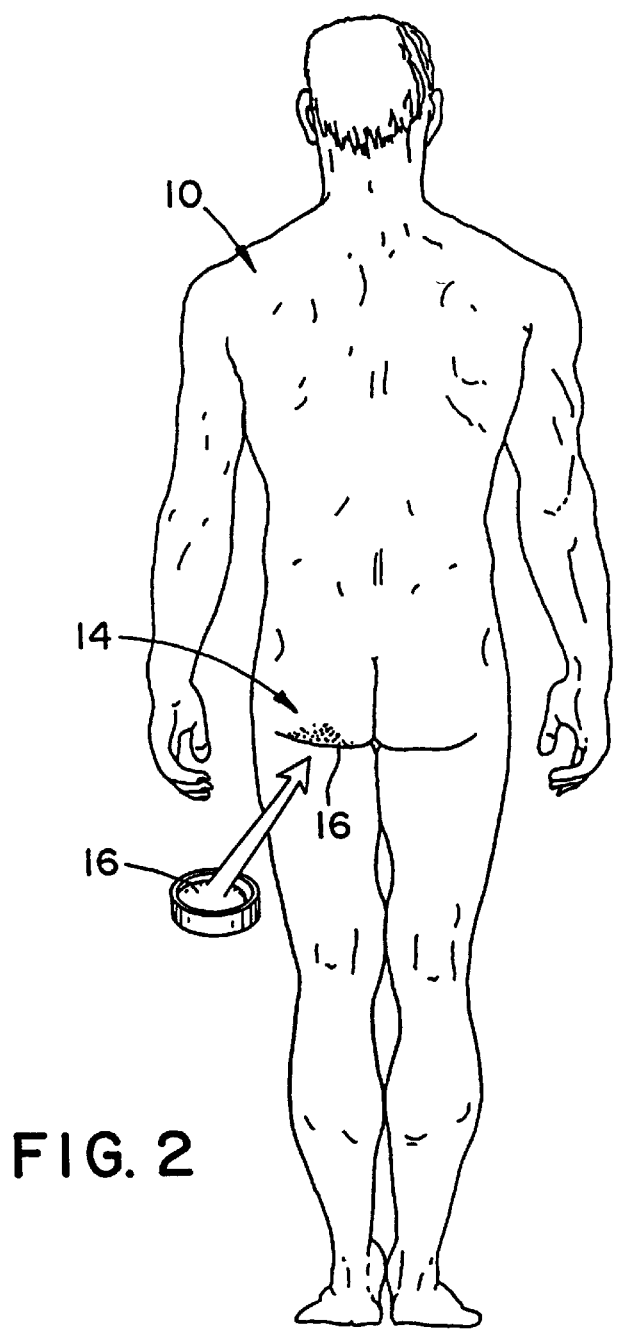

FIG. 2 illustrates the same patient 10 with an acne-affected area 14 with an agent which affects muscarinic receptors, such as neostigmine, optionally admixed with lecithin, and applied topically in either a gel or a cream.

As a specific example, 2 mg of neostigmine and 2700 mg of lecithin may be mixed with 120 cc of a topical gel. Again the neostigmine/lecithin is initially provided in solution as 0.0168 mg/cc and with the resultant mixture 16 comprising 2 mg of neostigmine in a total of 120 cc. The resultant set or cream is applied to the acne-affected area 14 whereby 0.1 mg of neostigmine covers an area of approximately 6×6 square inches.

DETAILED DESCRIPTION OF THE INVENTION

The present invention is based at least in part on the surprising discovery that the topical, non-systemic, and preferably, non-transdermal, application of muscarinic agents is effective in significantly reducing, and therefore, treating acne in patients in need of such treatment. The prototypical muscarinic agent is neostigmine, but other muscarinic agents include, but are not limited to, compounds based on or derived from pharmaceutically acceptable salts, prodrugs, and derivatives thereof. Examples of preferred compounds which are specifically contemplated as muscarinic agents suitable for use in accordance with the present invention include, but are not limited to, e.g., the muscarinic receptor agonists (e.g., acetylcholine and synthetic choline esters, and cholinomimetic alkaloids, e.g., pilocarpine, muscarine, and arecoline and their synthetic congeners), and the anticholinesterase agents disclosed in chapters 7 and 8 of Goodman and Gilman, The Pharmacological Basis of Therapeutics, $9^{th}$ ed., McGraw Hill, New York (1996) (which is hereby incorporated by reference as though set forth in full herein) in particular, neostigmine.

Other compounds specifically contemplated include muscarinic antagonists. Pharmaceutically acceptable salts of the foregoing compounds may also be employed. It is expected that as the field of research in the present area expands, new muscarinic agents will be discovered. It is expected that such muscarinic agents will be effectively used in accordance with the present invention.

Surprisingly, it has been found that, analogously to the topical analgesic effectiveness of muscarinic analgesic agents disclosed in U.S. application Ser. No. 09/083,431, topical application to skin of agents which bind to muscarinic receptors is effective in treating acne in a patient suffering therefrom in the absence of delivery of clinically effective central nervous system levels. These muscarinic receptor effects, which are more pronounced in inflamed than in non-inflamed tissues, are a considerable advantage considering that most acne is associated with inflammation. The work disclosed in Ser. No. 09/083,431 demonstrated that extremely small systemically inactive doses of muscarinic drugs such as neostigmine can produce potent analgesic effects after local application to skin. Unexpectedly, similar beneficial effects are found for topical treatment of acne with agents which bind to muscarinic receptors as well.

Also surprisingly, it has been found that, analogously to the topical effectiveness of opioid analgesic agents in treating acne disclosed in U.S. application Ser. No. 08/874,254, topical application to skin of agents which bind to muscarinic receptors is effective in treating acne in a patient suffering therefrom in the absence of delivery of clinically effective central nervous system levels.

Also surprisingly, similarly to the results found for opioid analgesic agents in U.S. patent application Ser. No. 09/083,431, application of agents which bind to muscarinic receptors in intact, non-inflamed skin in a patient suffering from non-inflammatory acne is potentiated by the use of skin-specific penetration enhancers, which are added to the topical formulation, whereby even acne on non-inflamed skin can be successfully treated with topical agents which affect peripheral muscarinic receptors in the absence of delivery of clinically effective central nervous system levels. Moreover, these skin penetration enhancers surprisingly improve the effectiveness of agents which affect peripheral muscarinic receptors in the treatment of acne in inflamed skin without the concomitant delivery of substantial amounts of the agent into the central nervous system. The anti-acne effect is thus potentiated by topically administering to a patient in need of such treatment a topically effective amount of a muscarinic agent, which amount is systemically ineffective, admixed with a skin-specific penetration enhancer, such as, e.g., lecithin, and a pharmaceutically acceptable excipient for topical administration, preferably whereby effective treatment of the inflamed or, in particular, non-inflamed, acne-affected skin is induced in the substantial absence of transdermal delivery of an effective amount of the muscarinic agent to the central nervous system.

The choice of topical excipient as a vehicle for the anti-acne agent, while routine, is a significant consideration in the present invention for reasons which follow. An important criterion for selecting suitable topical excipient is that it should not enhance the delivery of the muscarinic agent to the systemic circulation, e.g., transdermal transmission. As used herein, the term non-transdermal carrying agent is defined as a vehicle into which the muscarinic agent is diluted, which vehicle will not significantly enhance the migration of the muscarinic agent through the skin. Thus, non-transdermal carrying agents do not enhance the systemic delivery of the muscarinic agent. An additional consideration is that the excipient preferably will not exacerbate the acne condition. Preferred non transdermal carrying agents include, but are not limited to, K-Y Gel™ or K-Y Jelly™, Eucerine™, lanolin, Vaseline™, and Aquaphor™. All of these non-transdermal carrying agents are contrasted with transdermal carrying agents such as DMSO, which can significantly enhance penetration and/or migration of a drug through the skin and thus the systemic delivery of the drug. A thorough description of acceptable pharmaceutical carrying agents can be found in many pharmaceutical science textbooks, including, for example, *Remington's Pharmaceutical Sciences, Eighteenth Edition,* (Mack Publishing Company 1990), the entire contents of which are hereby incorporated by reference as though set forth herein.

Additionally, acne may be treated in accordance with the present invention by administering the muscarinic agent suspended in or admixed with a suitable non-transdermal carrying agent and sprayed (either with a manually-actuated pump or with the aid of a suitable pharmaceutically-acceptable propellant) onto the affected skin of the patient in need of treatment. Suitable formulations for topical application of drugs by spraying the formulation containing the drug onto the skin are well known to those of ordinary skill in the art and can be routinely selected.

Additionally, acne may be treated in accordance with the present invention by administering the muscarinic agent suspended in or admixed with a suitable non-transdermal carrying agent which may further include transdermal enhancers, as defined below.

The topical application of muscarinic agents in accordance with the present invention reduces acne lesions. Therapeutic effects of the present invention include, but are not limited to, decrease in redness and swelling of the affected area, reduction in the number of lesions in the affected area, and a general decrease in local inflammation. A primary advantage of the present invention is the excellent improvement in the condition without the typical side effects of conventional therapies. The potential for the present invention is widespread and the topical application of muscarinic agents shows promise as an exciting new method of acne treatment which does not exhibit the side effects associated with the prior art treatments.

While not wishing to be bound by theory, it is believed that the present invention may involve the interaction between the applied muscarinic agent and muscarinic receptors analogous to those proposed for the effect of opioid analgesic agents on white blood cells. The present scientific literature does not explain the practical role of the such opioid receptors on white blood cells. Their presence has been demonstrated in vitro (see *Advances in Neuroimmunology* Vol. 4, pgs. 69–82 (1994), cited above and incorporated by reference), but their practical function is still unknown. In fact, unlike opioid receptors in the nervous system, an endogenous ligand for opioid receptors on white blood cells has not yet been identified. Therefore, their function on white blood cells is believed to be quite different from their function in the nervous system. From the results presented herein, it appears that the opioid receptors on white blood cells may be involved in mediating an immune response. For these reasons, the present invention is not only useful in the treatment of acne, but is also useful in the treatment of local inflammation of the skin, such as Staphylococcus infections and other localized skin infections, as well as burns, insect bites and stings, and superficial wounds.

It has surprisingly been found that treatment of suitable conditions in accordance with the present invention results in improved healing of the condition. For example, when used in the treatment of acne, lesions which are treated disappear faster than when left untreated, the size of the lesions decreases more rapidly and redness in the area is more rapidly diminished as well. Normally herpetic lesions can take as long as 20 days to disappear without treatment. Very few treatments known in the art can decrease the healing time of herpetic lesions (decrease the time to remission). When treated in accordance with the present invention, however, herpetic lesions dry up more rapidly, stop oozing and forming pus sooner, and generally disappear more rapidly than when left untreated. In accordance with the present invention, healing time of herpetic lesions can be reduced to as little as 7 days.

These unexpected improvements in healing in accordance with the present invention appear to contradict what is known in the art, at least for opioids. For example, Peyman et al. demonstrate that epithelial wound closure in the cornea is not significantly different when the wound is treated with saline, or if the wound is treated with morphine sulfate (Br. J. Ophthalmol. (1994) Vol. 78, pgs. 138–141).

The following definitions in this specification are intended to be interpreted in an illustrative, rather than limiting sense. Therefore, they are to be interpreted inclusively, and are not to be limited to the specific definition recited.

A. Definitions

Agonist: a compound that displays an affinity for a receptor, and which enhances or stimulates the functional properties of the receptor. Examples of muscarinic agonists include but are not limited to, muscarinic receptor agonists (e.g., acetylcholine and synthetic choline esters, and cholinomimetic alkaloids, e.g., pilocarpine, muscarine, and arecoline and their synthetic congeners), and anticholinesterase agents, in particular, neostigmine.

Analgesia: relief of pain.

Analgesic: a compound that relieves pain; a muscarinic analgesic relieves pain by action on muscarinic receptors.

Antagonist: a compound that does not enhance or stimulate the functional properties of a receptor, yet block those actions by an agonist.

Bandage: a dressing used to cover an afflicted area.

Centrally-mediated analgesia: analgesia produced through activation of muscarinic receptors in the central nervous system (brain, spinal cord, epidural space, etc.)

Central muscarinic receptor: muscarinic receptor that is found in the central nervous system.

Central nervous system: the brain and spinal cord.

Dermal: relating to the dermis.

Dressing combine: designed to provide warmth and protection to absorb large quantities of fluid that may drain from an incision or wound; consists of a nonwoven fabric cover enclosing fiber with or without absorbent tissue.

Inflammation: an immune system-mediated process characterized by redness, heat, swelling, and pain at the local site.

Mixed agonist-antagonist: referring to muscarinic agents, a compound which displays both agonist and antagonist activities at muscarinic receptors.

Muscarinic agent: agents which interact with muscarinic receptors; muscarinic agents may be muscarinic receptor agonists, muscarinic receptor partial agonists, or muscarinic receptor mixed agonist-antagonists.

Muscarinic receptor: a receptor at which a muscarinic agent binds.

Partial agonist: a compound which produces some effects, but not others, at receptor subtypes which are known to be responsible for multiple effects.

Perineurium: the sheath of dense connective tissue that envelops a bundle of nerve fibers composing a peripheral nerve.

Peripheral nervous system: cranial, spinal, and peripheral nerves which serve to provide a nervous connection between tissues and organs of the body and the brain.

Peripheral muscarinic receptor: muscarinic receptor located outside the central nervous system.

Sprouting: a phenomenon which occurs in inflammation which is characterized by an increase in the number of peripheral sensory nerve terminals as well as the number of peripheral muscarinic receptors.

Skin: the outer covering of an animal body; the outermost layer of skin is called the epidermis (non-living part), the layer beneath the epidermis called the dermis (living part).

Therapeutically-effective amount: the amount necessary to bring about a therapeutic effect.

Transdermal: passing through the dermis.

B. Additional Definitions

Muscarinic Agents: It is to be appreciated that all the present invention has been described primarily with reference to the use of neostigmine. Other muscarinic agents may be used to interact with the peripheral muscarinic receptors which are present in peripheral tissues in various areas of the body and the invention is not to be limited specifically to neostigmine.

Suitable muscarinic agents include compounds which have an effect through binding to any muscarinic receptor, whereby the anti-acne properties of the agent are effective, as well as agents which enhance the anti-acne properties of other agents which bind to muscarinic receptors. These include, e.g., the muscarinic receptor agonists (e.g., acetylcholine and synthetic choline esters, and cholinomimetic alkaloids, e.g., pilocarpine, muscarine, and arecoline and their synthetic congeners), and the anticholinesterase agents disclosed in chapters 7 and 8 of Goodman and Gilman, The Pharmacological Basis of Therapeutics, $9^{th}$ ed., McGraw Hill, New York (1996), in particular, neostigmine.

Topical Excipients: The choice of topical excipient as a vehicle for the muscarinic agent, while routine, is an important aspect of the claimed invention. The most important criterion for selecting a suitable topical excipient is that it does not enhance delivery of the muscarinic agent to the systemic circulation or to the central nervous system by substantial transdermal or transmucosal transmission. For example, in general, it is preferred that the topical excipient not have substantial occlusive properties, which enhance percutaneous transmission of the muscarinic agent through the skin or mucosa into the systemic circulation. Such occlusive vehicles include hydrocarbon bases such as white petrolatum (e.g., Vaseline); anhydrous absorption bases such as hydrophilic petrolatum and anhydrous lanolin (e.g., Aquaphor); and water-in-oil emulsion bases such as lanolin and cold cream.

More preferred are vehicles which are substantially nonocclusive, and generally include those which are water-soluble, such as oil-in-water emulsion bases (creams or hydrophilic ointments) and water-soluble bases such as polyethylene glycol-based vehicles and aqueous solutions gelled with various agents such as methylcellulose, hydroxyethyl cellulose, and hydroxypropyl methylcellulose (e.g., K-Y Gel).

Suitable topical excipients and vehicles can be routinely selected for a particular use by those skilled in the art, and especially with reference to one of many standard texts in the art, such as Remington's Pharmaceutical Sciences, Vol. 18, Mack Publishing Co., Easton, Pa. (1990), in particular Chapter 87.

Other additives, e.g., for enhancing the adherent properties of the pharmaceutical preparation to various special skin areas, e.g., the axillar, plantar and palmar skin, and mucosal tissues, e.g., in the mouth, on the throat, on the genitalia, particularly the external female genitalia, can be similarly routinely selected and the preparation adapted to such use by one of ordinary skill in the art.

Transdermal Enhancers: The most important criterion for selecting a suitable topical excipient is that, while it enhances percutaneous delivery of the muscarinic and, optionally, opioid analgesic agent into the skin, it does not enhance delivery of the muscarinic or opioid analgesic agent through the skin into the systemic circulation, e.g., it does not provide substantial transdermal transmission, and more particularly does not provide transmission to the central nervous system. In the case of some enhancers, the amount and rate of transmission and thus the difference between providing transdermal delivery and not doing so will lie in the selection of the amount of enhancer used, the intactness of the skin, the type of skin which is being treated, the nature of the muscarinic or opioid analgesic agent, etc. However, these are routinely determinable parameters which can be optimized for a particular condition by one of ordinary skill in the art.

Various methods have been used to increase skin permeation of drugs include penetration enhancers, prodrugs, superfluous vehicles, iontophorosis, phonophoresis and thermophoresis. In particular, penetration enhancers are preferred.

Ideal penetration enhancers have no irritancy or toxicity to the skin, as well as high enhancing effects, and do not further aggravate acne lesions. Enhancers themselves should be physiochemically stable and not have pharmacologic effects and preferably should not have smell, color or taste.

The stratum corneum provides the principal barrier to the percutaneous penetration of topically applied substances. It is the most superficial, cutaneous layer, the horny layer, which consists of flat, scalelike "squames" made up of the fibrous protein keratin. The squames are continually being replaced from below by epidermal cells that die in the process of manufacturing keratin. It is unlikely that the emulsified fat on the skin surface greatly affects permeability. However, vehicles can control, to a great extent, the rate of penetration of drugs that are applied to the skin. The intercellular lipids may be important for the permeability barrier in skin.

It is known that some combinations of enhancers are synergistic in action, as with ethanol as a vehicle for the potent enhancer laurocapram. Some combinations are not synergistic; for instance, (N) decylmethylsulfoxide lowers the zeta potential of the skin; thus, enhancement due to conduction flow (iontophoresis) is minimized. In any case, optimization of suitable transdermal enhancing preparations for a given use is routine for one of ordinary skill in the art.

Thus, suitable topical transdermal enhancing agents can be routinely selected for a particular use by those skilled in the art, and especially with reference to one of many standard texts in the art, such as Remington's Pharmaceutical Sciences, Vol. 18, Mack Publishing Co., Easton, Pa. (1990), in particular Chapter 87. For example, suitable enhancers for transdermal absorption include ethanol, propylene glycol, water, sodium oleate, leucinic acid, oleic acid, capric acid, sodium caprate, lauric acid, sodium laurate, neodecanoic acid, dodecylamine, cetryl lactate, myristyl lactate, lauryl lactate, methyl laurate, phenyl ethanol, hexamethylene lauramide, urea and derivatives, dodecyl N, N-dimethylamino acetate, hydroxyethyl lactamide, phyophatidylcholine, sefsol-318 (a medium chain glyceride), isopropyl myristate, isopropyl palmitate, several surfactants, including polyoxyethylene (10) lauryl ether (Brij 361 R), diethyleneglycol lauryl ether (PEG-2-L), laurocapram (Azone; 1,1-dodecylazacycloheptan-2-one), acetonitrile, 1-decanol, 2-pyrrolidone, N-methylpyrrolidone, N-ethyl-1-pyrrolidone, 1-methyl-2-pyrrolidone, 1-lauryl-2-pyrrolidone, sucrose monooleate, dimethylsulfoxide (DMSO) about 80% concentration required, decylmethylsulfoxide (n) enhances primarily polar or ionic molecules (soluble in ethanol), acetone, polyethylene glycol 100–400 MW, dimethylacetamide, dimethylforamide, dimethylisosorbide, sodium bicarbonate, various $N_{7-16}$-alkanes, mentane, menthone, menthol, terpinene, D-terpinene, dipentene, N-nonalol and limonene.

Skin-specific penetration enhancer: an agent which enhances the penetration of a muscarinic agent which affects peripheral muscarinic receptors through the uppermost layers of non-inflamed skin to the skin layers in which the peripheral nerves are located that are involved in acne, without substantial transmission or delivery to the CNS. In some cases, the skin-specificity of the penetration enhancer will be determined by its concentration; e.g., at a concentration of 22%, lecithin has been shown to be an excellent vehicle for enhancing transdermal delivery to the systemic circulation, whereas it has been shown that at a concentration of 3–6% in non-inflamed skin, lecithin potentiates the passage of analgesics, e.g., morphine sulfate, across the epidermis into the dermis, yet very little, if any, of the active agent is carried beyond those two layers into the bloodstream. Similarly, at concentrations of 3–6%, lecithin can enhance transport of morphine sulfate across the epidermis and into the dermis in inflamed skin, without transport of substantial amounts into the systemic circulation. Similar optimization can be routinely determined by the skilled worker for agents which affect peripheral muscarinic receptors, e.g., a concentration of 3–6% lecithin for enhancing transport of neostigmine across the epidermis and into the dermis without transport of substantial amounts into the CNS.

Directly activate peripheral muscarinic receptors in the skin, but not sufficient to activate central nervous system muscarinic receptors: what is meant by this phrase is that the action of the muscarinic agent is mediated through interaction with peripheral muscarinic receptors, e.g., and not through interaction with CNS receptors. See, e.g., Stein (1993), supra, which sets forth criteria for evaluating peripheral opioid receptor antinociception, as an example for such evaluation.

Substantial absence of transdermal delivery or does not enhance transdermal delivery of the muscarinic agent: what is meant by this phrase is that upon the induction of an anti-acne effect, less than 25%, preferably less than 10%, more preferably less than 5%, still more preferably 1% and most preferably none of the muscarinic agent has passed through the stratum corneum into the systemic circulation. In particular, an insufficient amount for induction of systemic activity is delivered to the systemic circulation.

Other terms employed herein not specifically defined immediately above are well known to those of ordinary skill in the art and/or are also further defined in the specification either expressly or indirectly.

C. Illustrative Preferred Embodiments

The present invention is directed to methods of treating acne using topical muscarinic agents. In accordance with the present invention, muscarinic agents are preferably applied topically to an area which is affected by acne. Preferably, the application of muscarinic agents in accordance with the present invention results in a reduction in the number and severity of the acne lesions.

In accordance with the present invention, the muscarinic agents of choice may be an agonist, a mixed agonist/antagonist, or a partial agonist. Preferably the muscarinic agent used in accordance with the present invention comprises a muscarinic agonist. Muscarinic agonists include, but are not limited to, These include, e.g., the muscarinic receptor agonists (e.g., acetylcholine and synthetic choline esters, and cholinomimetic alkaloids, e.g., pilocarpine, muscarine, and arecoline and their synthetic congeners), and the anticholinesterase agents disclosed in chapters 7 and 8 of Goodman and Gilman, (1996), ibid, in particular, neostigmine, and mixtures of the foregoing.

In other preferred embodiments, the muscarinic agent selected comprises a compound with mixed muscarinic agonist/antagonist activities, or one that exhibits only partial agonist activity. In other preferred embodiments, the muscarinic agent selected may comprise an muscarinic antagonist.

Other preferred embodiments envisioned include, but are not limited to, natural and synthetic peptides which interact with muscarinic receptors. The present invention is not limited to the delivery of a single muscarinic agent: preferred embodiments include mixtures of muscarinic agents. The present invention is also not limited to the specific drugs mentioned herein, and derivatives that are pharmaceutically-acceptable salts, prodrugs, and other derivatives are envisioned as well. It is expected that, as medical science advances, more compounds which can be classified as muscarinic agents will be discovered. Such compounds are also envisioned to be within the scope of the present invention. The present invention is not limited solely to the delivery of muscarinic agents: other agents may be incorporated as well, including but not limited to antibiotics and/or steroids.

As noted above, the doses of muscarinic agents used in accordance with the present invention are much smaller than those doses normally used for central or system effects. Specifically, the present invention uses doses of muscarinic agents that are considerably lower than doses of intravenously (IV) administered muscarinic agents which are given for reversal of curare muscle relaxation during surgery. Doses used in accordance with the present invention preferably range from about 1/1000th of the IV dose to about 1/10th of the IV dose. More preferably, doses range from about 1/500th of the IV dose to about 1/20th of the IV dose. Most preferably, doses administered in accordance with the present invention are about 1/100th of the IV dose administered to achieve a centrally-mediated effect. For example, neostigmine is normally administered as 0.1 mg/kg IV to achieve the effect of reversing curare muscle relaxation. In accordance with the present invention, a preferred dose of neostigmine would be about 5–10 µg per square inch of affected area.

It should be recognized that not all muscarinic agents are equipotent, i.e., the do not all result in the same degree of potency for the same mass of drug. Therefore, when choosing the amount of muscarinic agent to be used in accordance with the present invention, the amount selected is preferably equipotent to the doses of neostigmine presented herein. Although it is not believed that the analgesic effect of the neostigmine used is an important part of the present invention, using equianalgesic doses has proven to be effective in choosing doses for practicing the present invention. Equianalgesic doses for opioids, as a comparison, are well known to those of ordinary skill in the art. In addition, one of ordinary skill in the art would be readily able to determine how to use other muscarinic agents by following the present disclosure.

Regardless of which muscarinic agent is used in accordance with the present invention, a preferable dose is that which produces a therapeutic effect. Different muscarinic agents will likely be used in different amounts, and even according to different administration schedules. In accordance with the present invention, a muscarinic agent may be applied only once daily in a higher dose, or several times daily in a lower dose. Alternatively, it may be determined that a therapeutic effect can be achieved by the administration of a lower dose only once daily. For other patients, a higher dose administered several times daily may be necessary. Many combinations of dose and administration schedule are acceptable within the scope of the present invention. The only requirement is that the dose be delivered in a schedule which produces a therapeutic effect. Of course, the lower limit for administration is that which will produce a therapeutic effect.

In addition, the muscarinic agents present invention can be used in conjunction with topically applied opioid analgesic and anti-acne agents, e.g., in accordance with the inventions described in U.S. Pat. No. 5,589,480 and U.S. Ser. No. 08/874,254. Examples of such analgesic agents include, but are not limited to morphine, cyclazocine, piperidine, piperazine, pyrrolidine, morphiceptin, meperidine, trifluadom, benzeneacetamine, diacylacetamide, benzomorphan, alkaloids, peptides, phenantrene and pharmaceutically acceptable salts, prodrugs or derivatives thereof. Specific examples of compounds contemplated by as suitable in the present invention include, but are not limited to morphine, heroin, hydromorphone, oxymorphone, levophanol, methadone, meperidine, fentanyl, codeine, hydrocodone, oxycodone, propoxyphene, buprenorphine, butorphanol, pentazocine and nalbuphine. As used in the context of opioid agents herein, "pharmaceutically acceptable salts, prodrugs and derivatives" refers to derivatives of the opioid analgesic compounds that are modified by, e.g., making acid or base salts thereof, or by modifying functional groups present on the compounds in such a way that the modifications are cleaved, either in routine manipulation or in vivo, to produce the analgesically active parent compound. Examples include but are not limited to mineral or organic salts of acidic residues such as amines, alkali or organic salts of acidic residues such as carboxylic acids, acetate, formate, sulfate, tartrate and benzoate derivatives, etc. Suitable opioid analgesic agents, including those specifically mentioned above, are also described in Goodman and Gilman, ibid, chapter 28, pp. 521–555.

In addition, other active agents may be included in the pharmaceutical composition, e.g., topically-effective anaesthetics such as xylocaine, cocaine, lidocaine, benzocaine, etc., which may provide a more immediate, if less effective in the long run, level of pain relief until the analgesic agent becomes fully effective. Other active agents which may be present in the pharmaceutical preparations include, e.g., antibiotics, and especially those agents which themselves cause pain when applied to the inflamed site due to their inherent properties, e.g., pH.

Still other agents can also be administered, preferably topically, to potentiate the effects of the topically-administered muscarinic and/or opioid analgesic agents. For example, dextromethorphan, a non-addictive opioid compound, can be co-administered, preferably topically, although parenteral administration is also effective, to enhance the effectiveness of the topically administered agent. Without wishing to be bound by theory, it is believed that dextromethorphan has previously unappreciated analgesic properties in peripheral nerves. Suitable concentrations of dextromethorphan are routinely ascertainable by the skilled worker, and include the normal therapeutic amounts administered parenterally for conventional purposes, e.g., as a cough suppressant, or less, and routinely determinable amounts for topical administration; for example, 1 g of dextromethorphan can be added to a composition disclosed herein to provide additional acne-effective treatment.

Certain embodiments of the present invention comprise any topically acceptable non-transdermally effective carrier vehicle. Preferred topically acceptable vehicles include but are not limited to gels, lotions, creams, ointments, and liquids. Administration of the preferred embodiment is performed in accordance with that mode which is most amenable to the topically acceptable form chosen. For example, gels, lotions, creams and ointments are preferably administered by spreading. Liquids are preferably administered by spraying.

Although it is not crucial, the dilution of the muscarinic agent in the carrier vehicle can be an important consideration as well. The muscarinic agent concentration in the vehicle should be high enough that the patient does not need to wait an excessively long time for the vehicle to dry. On the other hand, the muscarinic agent concentration should be dilute enough that a patient can achieve effective coverage of the affected area. Suitable vehicles include aqueous creams and alcoholic sprays (e.g., sprays comprising alcoholic solutions) or gels. Additionally, the vehicle could include a component which polymerizes in response to exposure to air or ultraviolet radiation.

The amount of vehicle to be applied will vary depending on the choice of vehicle as well. For example, when the muscarinic agent is administered by spraying an alcoholic liquid solution of the drug, the total volume in a single dose may be as low as 0.1 ml. Conversely, when the muscarinic agent is administered in an aqueous cream, the total volume may be as high as 1 ml. It has been found that a total volume for application of K-Y Jelly™ is preferably about 0.5 ml/in$^2$ of skin. Of course, if a large contiguous area is affected, a larger application volume may be necessary. Conversely, if the acne lesions are scattered, the volume applied may be smaller. The carrier selected and its manner of application are preferably chosen in consideration of the needs of the patient and the preferences of the administering physician.

In accordance with the present invention, a muscarinic agent preparation is applied to the affected area regularly until relief is obtained. Preferably, such regular application comprises application from one to five times per day. However, other application schedules may be utilized in accordance with the present invention.

Other embodiments of the present invention include dressings that may be placed on the affected area and remain there to release muscarinic agent onto the affected area. Preferably, such embodiments include but are not limited to, bandages, surgical dressings, gauzes, patches, and sterile adhesive strips. Preferred dressings are treated with muscarinic agents prior to application to the affected area. The dressing preferably acts as a protective barrier to the area, preventing the muscarinic agent from being wiped away. Such embodiments are especially useful for overnight application to an affected area. However, these preferred embodiments might also find application in daily use. Preferred dressings may be pretreated with muscarinic agents by a manufacturer and packaged as ready to use. Alternatively, a subject may apply a gel, cream, lotion or ointment prepared in accordance with the present invention to a dressing which is then applied to the affected area.

When administered in accordance with the present invention, treatment will result in therapeutic effects which include an anti-acne effect. Therapeutic effects in the affected area include, but are not limited to, decrease in redness, decrease in swelling, and decrease in inflammation. When a muscarinic preparation is used, therapeutic effects in the affected area include decrease in pain. These therapeutic effects are observed when treatment in accordance with the present invention is made to any of the suitable conditions.

The present invention is not limited to the treatment of acne vulgaris and is also directed to the treatment of neonatal and infantile acne, perioral dermatitis, acne conglobata, hidradenitis suppurative, acne filminans, pyoderma faciale, acne excorieé des jeunes filles, acne mechanica, acne tropicalis, acne aestivalis, favré-racouchot syndrome, drug-induced acne, acne cosmetica, pomade acne, occupational acne, chloracne, steroid acne, rosacea, acne keloidalis nuchae and gram-negative folliculitis. The procedures followed for treatment of these diseases are the same as those set forth for the treatment of acne vulgaris set forth herein. The present invention is also useful in the treatment of other conditions in which local inflammation or local infection are present. Such other conditions include Staphylococcus infections, various herpes and other viral infections, and burns. Local inflammation which is the result of noxious stimuli include irritation and inflammation resulting from contact with chemicals or other irritants. Inflammation resulting from contact with poison ivy, or other plants, is also treatable in accordance with the present invention. Other sources of inflammation treatable in accordance with the present invention include stings from insects.

The foregoing specific embodiments are illustrative of applications in which methods of treating acne using muscarinic agents in accordance with the present invention can be employed. Those of ordinary skill in the art will readily understand that other manners of administration of muscarinic agents to treat acne are suitable and are in accordance with the present invention as well.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the foregoing and in the following examples, all temperatures are set forth uncorrected in degrees Celsius; and, unless otherwise indicated, all parts and percentages are by weight.

The entire disclosures of all applications, patents and publications, cited above and below, including U.S. Ser. No. 08/291,614, filed Aug. 17, 1994, now U.S. Pat. No. 5,589,480, U.S. Ser. No. PCT/96/19618, filed Dec. 12, 1996, U.S. Ser. No. 08/874,254, U.S. Ser. No. 09/028,117, filed Jan. 23, 1998, and U.S. Ser. No. 09/083,431, filed May 29, 1998, are hereby incorporated by reference.

EXAMPLES

Representative examples of tests of the invention are set forth in the Examples. In particular, patients with various types of acne who had tried several different treatments including benzoyl peroxide, tretinoin, and antibiotics, were quite distraught with their appearance. These patients were treated with various treatment regimens, all with unexpected, surprisingly quite good results.

Example 1

A 15 Year Old Male With Acne Unresponsive to Usual Over-the-counter Medications

The patient was given 15 cc of a mixture of gel with 625 mcg of neostigmine. The patient was instructed to use it 3 times a day. The next morning patient saw a difference already and within 3 days he had 100% relief from acne. No side effects were reported.

Example 2

A 32 Year Old Female With Severe Acne Unresponsive to Other Over-the Counter-Treatment The patient was enrolled in the trial of neostigmine for treatment of acne. She received 15 cc of gel with 625 mcg of neostigmine to be used 3 times a day. Within 2 days 80% of redness had disappeared. No side effects were reported.

Example 3

A 38 Year Old Female With Acne Unresponsive to Other Over-the-counter Medications The patient was provided with 15 cc of gel with 625 mcg of neostigmine to be applied topically 3 times a day. She had 70% disappearance of the acne within 2 days. No side effects were reported.

Example 4

A 14 Year Old Female With History of Acne Unresponsive to Usual Treatment of Acne The patient was provided with 15 cc gel of 625 mcg of neostigmine to be used three times daily. The patient reported 75% improvement with 2 days of treatment. No side effects were reported.

Example 5

A 14 Year Old Female with Facial Acne Unresponsive to Usual Treatments

The patient was provided with 15 cc of gel with 625 mcg of neostigmine. The patient reported 50% improvement within 2 days of treatment. No side effects were reported.

Example 6

A 16 Year Old Female With History of Acne Unresponsive to Usual Treatment

The patient was provided with 15 cc of gel with 625 mcg of neostigmine. After 2 days she reported 70% improvement in symptoms. No side effects were reported.

All of the foregoing acne patients treated according to the present invention I) stated the following: 1) The medication was only applied two or three times daily. The amount used was enough to cover the affected area and not more. 2) Starting at the point the treatment was initiated, growth of the lesion ceased. 3) In cases of mild-to-moderate acne, the lesions dried quickly, and disappeared within two to three days. 4) In cases of moderate-to-severe acne, the lesions reduced in redness swelling by about 50% within two to three days. 5) No side effects were observed from the treatment, including no itching and no peeling. Patients unanimously stated that the treatment according to the present invention was a significant improvement over their previous treatment because relief of the condition was observed without the side effects of other treatments. In addition, relief of the symptoms was more rapid when treated in accordance with the present invention.

From the foregoing Examples, it is clear that the use of muscarinic agents in accordance with the present invention can improve the healing of acne. A decrease in the number of lesions, redness, and swelling, is apparent more rapidly than when the lesions are left untreated or when the lesions are treated with over-the-counter preparations. Generally, treatment in accordance with the present invention will result in a shortened healing time.

From the foregoing descriptions, one skilled in the art can easily ascertain the essential characteristics of this invention, and without departing from the spirit and scope thereof, can make various changes and modifications to the invention to adapt it to various usages and conditions. Specifically, the foregoing can be applied to similar diseases (such as Staphylococcus infections and other skin inflammation) by following the foregoing procedures and applying routine standard pharmacological protocol.

Although the invention has been described with reference to particular embodiments, it is to be appreciated that various adaptations and modifications may be made and the invention is only to be limited by the appended claims.

What is claimed is:

1. A method of treating acne in a patient in need of such treatment, comprising topically administering a therapeutically effective amount of a composition comprising a muscarinic agent.

2. A method of claim 1, wherein said composition comprises a gel or cream.

3. A method of claim 2, wherein said gel or cream is administered by spreading the gel or cream on the affected area.

4. A method of claim 1, wherein said composition comprises a liquid.

5. A method of claim 4, wherein said liquid is administered by spraying onto the affected area.

6. The method of claim 1, wherein the muscarinic agent is administered in an amount equivalent to up to 100 $\mu$g of neostigmine per 6 $in^2$ of skin.

7. The method of claim 6, wherein the muscarinic agent is administered in an amount equivalent to up to 50 $\mu$g of neostigmine per 6 $in^2$ of skin.

8. The method of claim 1, wherein the muscarinic agent comprises neostigmine.

9. The method of claim 1, wherein a unit dose of said muscarinic agent is in the range of about 1/1000th of an effective intravenous dose of said muscarinic agent to about 1/10th of an effective intravenous dose of said muscarinic agent.

10. The method of claim 1, wherein a unit dose of said muscarinic agent is in the range of about 1/100th of an effective intravenous dose of said muscarinic agent to about 1/50th of an effective intravenous dose of said muscarinic agent.

11. The method of claim 1, wherein the acne comprises inflammatory acne.

12. The method of claim 1, wherein the acne comprises non-inflammatory acne.

13. A method of treating skin disorders involving sebaceous glands and follicles in a patient in need of such treatment, comprising applying a therapeutically effective amount of a composition comprising a muscarinic agent.

14. A method of claim 1, wherein administration is via a topical dressing.

15. A method of claim 1, wherein treatment is accomplished in the substantial absence of transdermal delivery of the muscarinic agent.

16. A method of claim 15, wherein said composition comprises a gel or cream.

17. A method of claim 16, wherein said gel or cream is administered by spreading the gel or cream on the affected area.

18. A method of claim 15, wherein said composition comprises a liquid.

19. A method of claim 18, wherein said liquid is administered by spraying onto the affected area.

20. The method of claim 15, wherein the muscarinic agent is administered in an amount equivalent to up to 100 $\mu$g of neostigmine per 6 $in^2$ of skin.

21. The method of claim 20, wherein the muscarinic agent is administered in an amount equivalent to up to 50 $\mu$g of neostigmine per 6 $in^2$ of skin.

22. A method of claim 13, wherein treatment is accomplished in the substantial absence of transdermal delivery of the muscarinic agent.

* * * * *